United States Patent [19]

Hamada et al.

[11] Patent Number: 5,684,169
[45] Date of Patent: Nov. 4, 1997

[54] CYCLODEXTRIN INCLUSION COMPLEX OF TAXOL, AND METHOD FOR ITS PRODUCTION AND ITS USE

[75] Inventors: Hiroki Hamada, Okayama; Kyoko Saito, Yokohama; Katsuhiko Mikuni, Yokohama; Nobuhiro Kuwahara, Yokohama; Hideki Takahashi, Yokohama, all of Japan

[73] Assignee: Ensuiko Sugar Refining Co., Ltd., Yokohama, Japan

[21] Appl. No.: 470,018

[22] Filed: Jun. 6, 1995

Related U.S. Application Data

[63] Continuation-in-part of Ser. No. 36,519, Mar. 24, 1993, and Ser. No. 234,678, Apr. 28, 1994, abandoned.

[30] Foreign Application Priority Data

Nov. 27, 1992 [JP] Japan .................................. 4-339495
Aug. 19, 1993 [JP] Japan .................................. 5-224999

[51] Int. Cl.⁶ .................................................. C07D 305/14
[52] U.S. Cl. ................................................ 549/510; 549/511
[58] Field of Search .................................... 549/510, 511

[56] References Cited

U.S. PATENT DOCUMENTS

| 3,459,731 | 8/1969 | Gramera et al. | 536/103 |
| 4,582,900 | 4/1986 | Brandt et al. | 536/103 |
| 5,024,998 | 6/1991 | Bodor | 514/58 |
| 5,126,333 | 6/1992 | Martini et al. | 514/58 |
| 5,160,727 | 11/1992 | Klohs et al. | 424/10 |
| 5,324,718 | 6/1994 | Loftsson | 514/58 |

FOREIGN PATENT DOCUMENTS

| 0 519 428 A2 | 12/1992 | European Pat. Off. |
| 0 519 428 A3 | 12/1992 | European Pat. Off. |
| 0 522 936 A1 | 1/1993 | European Pat. Off. |
| 0 522 937 A1 | 1/1993 | European Pat. Off. |
| 2 484 252 | 12/1981 | France |
| 4 028 004 A1 | 3/1981 | Germany |
| WO 91/04026 | 4/1991 | WIPO |
| WO 92/09589 | 6/1992 | WIPO |

OTHER PUBLICATIONS

D. Duchene, et al, "The Current State of β–Cyclodextrin in Pharmaceutics", (1990), pp. 1–6, *Acta Pharmaceutica*, vol. 36, No. 1.

Stu Borman, "Taxol To be Made from Renewable Materials by Organic Semisynthesis", Oct. 12, 1992, pp. 30–35, Chemical & Engineering News.

Gunda I. Georg, et al, "Synthesis of Biologically Active Taxol Analogues with Modified Phenylisoserine Side Chains", 1992, pp. 4230–4237, *J. Med. Chem.*, 35.

Francoise Guéritte–Voegelein, et al, "Relationships between the Structure of Taxol Analogues and Their Antimitotic Activity", 1991, pp. 992–998, *J. Med. Chem.*, 34.

Hamada et al AU 645927, Jan. 27, 1994, Derwent Abstract 94–074757.

*Primary Examiner*—Ba K. Trinh
*Attorney, Agent, or Firm*—Frishauf, Holtz, Goodman, Langer & Chick, P.C.

[57] ABSTRACT

There is provided an unbranched cyclodextrin or a branched cyclodextrin inclusion complex of taxol. The complex is produced by adding an unbranched cyclodextrin of a branched cyclodextrin to taxol at a molar ratio of 1–20 times with respect to taxol. A method is provided for the improvement of the solubility of taxol in water by adding an unbranched cyclodextrin or a branched cyclodextrin thereto at a molar ratio of 1–20 times with respect to taxol. The solubility of taxol in water is improved by the present invention. A cyclodextrin inclusion complex of taxol according to the present invention serves to make taxol more easily absorbed when administered to a cancer patient, which is beneficial to cancer patients and the physiological effects of taxol may therefore be more effectively induced.

19 Claims, 13 Drawing Sheets

CYCLODEXTRIN INCLUSION COMPLEX OF TAXOL, AND METHOD FOR ITS PRODUCTION AND ITS USE

This is a continuation-in-part application of application Ser. No. 08/036,519 filed Mar. 24, 1993 now abandoned and application Ser. No. 08/234,678 fled Apr. 28, 1994 now abandoned.

BACKGROUND OF THE INVENTION

1. Field of the Invention

The present invention relates to a method for improving the solubility of taxol in water, and more particularly, to a method for improving its water solubility by adding cyclodextrin or branched cyclodextrin (both sometimes referred to hereinafter as "CD") at a molar ratio of 1–20 times with respect to taxol to obtain a CD inclusion complex of taxol, thus improving the solubility of taxol in water and solubilizing taxol.

2. Background Information

Taxol is a substance which is extracted from the bark of a species of the North American yew tree (*Taxus brevifolia*), and it inhibits the division of cancer cells. Particularly, it is known to be effective for ovarian cancer patients, and has attracted attention as a novel and powerful anti-cancer agent. However, taxol does not dissolve in water, and thus is not absorbed when administered to patients.

SUMMARY OF THE INVENTION

It is an object of the present invention to provide a novel inclusion product of taxol having an improved solubility in water.

It is another object of the present invention to provide a method for producing a CD inclusion product of taxol in a convenient, economically advantageous manner, without the use of organic solvents.

Other objects of the invention will become apparent from the following description.

A purpose of the present invention is to overcome the above mentioned disadvantage of taxol.

As a result of varied and repeated research with the above in mind, the inventors of the present invention discovered that taxol can be solubilized by adding a CD thereto at a molar ratio of 1–20 times with respect to taxol, to improve the solubility of taxol in water. The present invention was completed on the basis of this discovery.

The present invention also provides the following:

(1) An inclusion product of taxol included in a substituted α-, β- or γ-CD, one or more hydroxyl groups of which are substituted through an ether bond with at least one member selected from the group consisting of methyl, hydroxyethyl and hydroxypropyl groups;

(2) A method for producing an inclusion product of taxol included in a CD, which method comprises reacting taxol with α-CD, β-CD, γ-CD or a substituted α-, β- or γ-CD, one or more hydroxyl groups of the substituted CD being substituted through an ether bond with at least one member selected from the group consisting of a glucosyl group, a maltosyl group, a maltooligosaccharide residue, a methyl group, a hydroxyethyl group and a hydroxypropyl group, and the reaction being conducted in an aqueous system, while stirring or shaking;

(3) A method for producing an inclusion product of taxol included in a CD, which method comprises reacting taxol with a substituted α-, β- or γ-CD, one or more hydroxyl groups of the substituted CD being substituted through an ether bond with at least one member selected from the group consisting of a methyl group, a hydroxyethyl group and a hydroxypropyl group, and the reaction being conducted in an organic solvent-water system, while stirring or shaking;

(4) A method for improving the solubility of taxol in water, which method comprises reacting taxol with α-CD, β-CD, γ-CD or a substituted α-, β- or γ-CD, one or more hydroxyl groups of the substituted CD being substituted through an ether bond with at least one member selected from the group consisting of a glucosyl group, a maltosyl group, a maltooligosaccharide residue, a methyl group, a hydroxyethyl group and a hydroxypropyl group, and the reaction being conducted in an aqueous system, while stirring or shaking; and (5) A method for improving the solubility of taxol in water, which method comprises reacting taxol with a substituted α-, β- or γ-CD, one or more hydroxyl groups of the substituted CD being substituted through an ether bond with at least one member selected from the group consisting of a methyl group, a hydroxyethyl group and a hydroxypropyl group, and the reaction being conducted in an organic solvent-water system, while stirring or shaking.

DETAILED DESCRIPTION OF THE INVENTION

Figure 1:
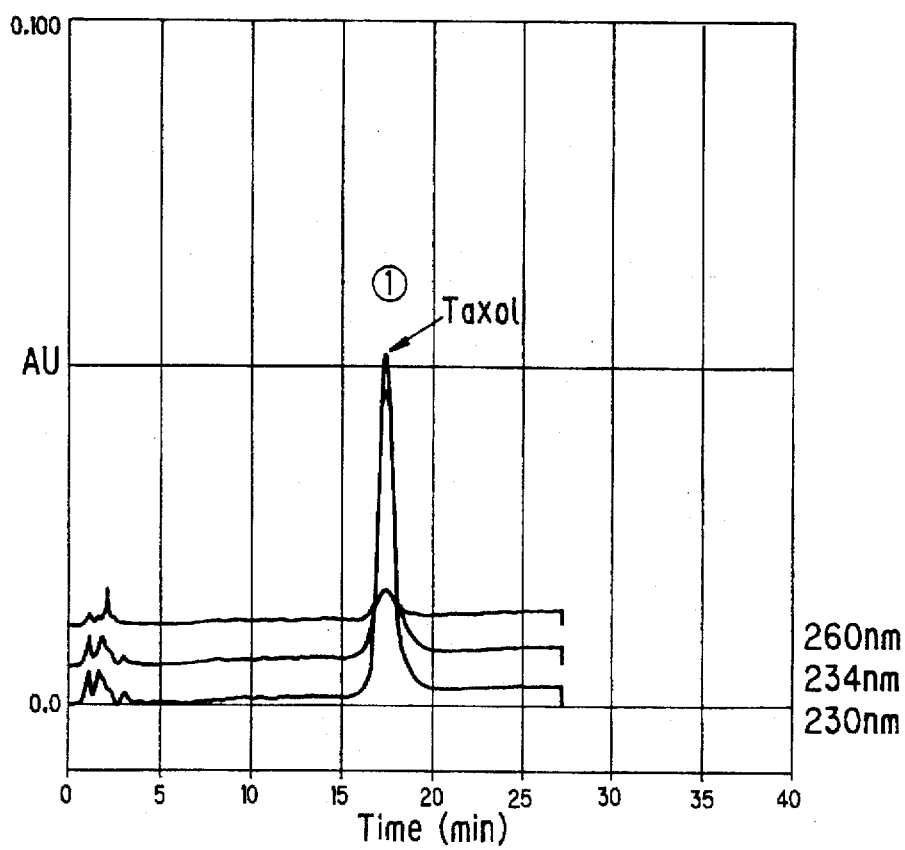
FIG. 1 shows an HPLC chromatogram of taxol.

The present invention provides a cyclodextrin or branched cyclodextrin inclusion complex of taxol, and further provides a method for the production of a cyclodextrin or branched cyclodextrin inclusion complex of taxol characterized by adding cyclodextrin or branched cyclodextrin to taxol at a molar ratio of 1–20 times with respect to taxol. The present invention also provides a method for the improvement of the solubility of taxol in water by adding cyclodextrin or branched cyclodextrin thereto at a molar ratio of 1–20, times with respect to taxol.

In an embodiment of the present invention, to obtain a CD inclusion complex of taxol, taxol can be first dissolved in an organic solvent. The organic solvent may be ethyl acetate, methanol, ethanol, acetone, etc., but methanol is particularly preferable. The amount of the organic solvent is not particularly limited so long as it dissolves the taxol.

On the other hand, an aqueous solution of CD is prepared in an amount of 1–20 times the molarity of the taxol, and is added to the taxol solution. In this case, stirring is generally preferred for complete mixing of the solution, and more preferably, a stirrer or the like is used for vigorous stirring. Also, there are no special conditions required regarding the reaction temperature, and the reaction may proceed adequately at room temperature. The reaction time may be from a few minutes to a few hours, and is normally from about 2 minutes to an hour.

Taxol is clathrated (or included) in the CD by this reaction.

By the term "CD" is meant a compound consisting of a ring of 6 to 8 D-glucoses linked by α-1,4 bonds. A CD consisting of 6 D-glucoses is referred to as α-CD. A CD consisting of 7 D-glucoses is referred to as β-CD. A CD consisting of 8 D-glucoses is referred to as γ-CD.

The CD used in the present invention may be α-CD, β-CD or γ-CD per se, or a substituted α-CD, β-CD or γ-CD, at least one of the hydroxyl groups of which is substituted with at least one functional group through an ether bond. Examples of substituted CDs for use in the present invention include those substituted with such functional groups as saccharide moieties (e.g., glucosyl, maltosyl or maltooligo-saccharide), alkyl groups (e.g., methyl or ethyl), hydroxyalkyl groups (e.g., hydroxyethyl or hydroxypropyl), and the like. Examples of substituted CDs for use in the present invention include glucosyl-α-CD, glucosyl-β-CD, glucosyl-γ-CD, maltosyl-α-CD, maltosyl-β-CD, maltosyl-γ-CD, maltotriosyl-α-CD, maltotriosyl-β-CD, maltotriosyl-γ-CD, etc. These CDs may be used alone or in a combination of two or more.

If the amount of CD added is less than the lower limit of 1:1 with respect to taxol, the solubility of taxol is not adequately increased, and if it is greater than 1:20, the excessive amount of CD does not contribute to inclusion complex formation.

In order to obtain a CD inclusion product of taxol by a reaction in an aqueous system, the CD is dissolved into water, and taxol is then added thereto, followed by vigorous stirring or shaking. The concentration of the CD can be from 0.0001 to 200% by weight, preferably from 1 to 50% by weight, based on the weight of water.

The CD is admixed in an amount of 1 to 100,000,000 times the mole amount of taxol, preferably 100 to 100,000 times the mole amount of taxol. The stirring or shaking is conducted as vigorously as possible for a period of from a few minutes to several tens of minutes. The reaction is carried out at a temperature of 0° to 60° C., preferably 15° to 40° C.

By the above reaction, taxol is included within the CD. When taxol is admixed at a high ratio, part of the compound may remain undissolved. In such a case, the undissolved compound can be removed from the reaction mixture by means of filtration.

The thus-obtained aqueous solution of the CD inclusion product of taxol can be dried; if necessary, to obtain powders of the inclusion product. The resulting CD inclusion product of taxol has a markedly improved solubility in water.

In order to obtain a CD inclusion product of taxol by a reaction in an organic solvent-water system (namely, a mixture of an organic solvent and water), taxol is first dissolved into an organic solvent.

Examples of organic solvents usable for the dissolution include ethyl acetate, methanol, ethanol, acetone, acetonitrile, tetrahydrofuran, dimethylsulfoxide, and the like. Methanol is particularly preferred. There is no particular restriction on the amount of organic solvents to be used, provided that taxol can be dissolved.

On the other hand, the CD is dissolved into water to prepare an aqueous solution containing the CD in an amount of 1 to 100,000,000 times, preferably 100 to 100,000 times the mole amount of the taxol, and the solution is added to the above taxol solution. Alternatively, the CD is added directly to a taxol solution. Upon the addition, the taxol solution is stirred, preferably in a vigorous manner using a stirrer or the like. There is no particular restriction on the temperature at which the inclusion reaction is carried out, and the reaction proceeds to a sufficient degree at room temperature. The reaction time can be in the range of from a few minutes to several hours.

By the above reaction, taxol is included within the CD.

In addition, if the solution is dried, a stable CD inclusion complex of taxol may be obtained, which is highly soluble in water.

A CD inclusion complex of taxol obtained in the above manner can be administered to a patient intravenously, orally or via another route. By such administration, a minute, but highly efficient dosage taxol may be provided to the patient. Thus, the physiological activity of taxol may be efficiently induced.

A CD inclusion complex of taxol obtained according to the present invention may be used in a variety of different forms. For example, it may be prepared as an injection drug or used as a powder without further processing, or the powder may be granulated, tableted or filled into capsules, etc., in a form as to best accommodate the patient. Of course, the inclusion product may also be used in the form of the original solution. Further, the same effects may be expected even if taxol is clathrated using a chemically modified CD such as hydroxypropyl CD.

Inclusion products of taxol according to this invention have a markedly improved solubility in aqueous phase and hence can be delivered in an effective manner to diseased body parts of patients suffering from cancer.

EXAMPLES

A more detailed explanation of the present invention will now be given with reference to the Examples, but the the present invention is not limited to these Examples.

Example 1

In this example, the influence of each type of CD on the solubilization of taxol was investigated.

First, 1 mg of taxol was dissolved in 2.0 ml of ethyl acetate. Meanwhile, each type of CD was dissolved in 2.0 ml of water to a molar ratio (taxol:CD) of 1:1, 1:5, 1:10 and 1:20, respectively. The CDs used were α-CD, γ-CD, maltosyl-α-CD, maltosyl-β-CD and maltosyl-γ-CD.

The taxol solution and the CD solutions were placed in test tubes each equipped with a ground-in stopper, and were then mixed by manual reciprocal shaking repeated 30 times. Next, the ethyl acetate layer was collected, and the absorbance was measured at 255 nm to calculate the amount of taxol which moved to the aqueous layer. The solubility of taxol was calculated by subtracting the solubility thereof when the CD was not dissolved in the aqueous layer (blank value), and the results are shown in Table 1. That is, since ethyl acetate used here moves to the aqueous phase and thus a minute amount of taxol dissolves therein even in a blank case where no CD is used, a solubility of 0.589 mg per 2 ml of water is obtained, and therefore this value has been subtracted from the solubilities listed in Table 1. The numbers in Table 1, then, represent the solubility of taxol increased by the addition of CD.

TABLE 1

Increased solubility of taxol in water using various CDs

| Molar ratio (taxol:CD) | 1:1 | 1:5 | 1:10 | 1:20 |
|---|---|---|---|---|
| α-CD | 0.067 | 0.036 | 0.213 | 0.186 |
| γ-CD | 0.045 | 0.050 | 0.315 | 0.319 |
| Maltosyl-α-CD | 0.048 | 0.102 | 0.106 | 0.208 |
| Maltosyl-β-CD | 0.036 | 0.017 | 0.120 | 0.132 |
| Maltosyl-γ-CD | 0.055 | 0.044 | 0.183 | 0.118 |

(mg per 2 ml of water)

The above results show that the solubility of taxol is improved by addition of a CD at a molar ratio thereto of 1:1 or greater. Also, with the exception of maltosyl-α-CD, an adequate effect was obtained with addition of a CD at a molar ratio of 1:10 or greater.

Further, of the various types of CDs, -γ-CD in particular produced significant improvement in the solubility of taxol, which indicated that it is the most appropriate substance for the solubilization of taxol.

Example 2

In this example, the solubility of a CD inclusion complex of taxol was determined in a more precise manner than in Example 1, and the influence of the organic solvent used to dissolve taxol was also investigated.

One milligram of taxol was dissolved in 2.0 ml of ethanol, and each type of CD was dissolved in 2.0 ml of water to a molar ratio (taxol:CD) of 1:1, 1:5, 1:10 and 1:20, respectively. The CDs used were α-CD, γ-CD, maltosyl-α-CD, maltosyl-β-CD and maltosyl-γ-CD.

The taxol solution and the CD solution were placed in a test tube equipped with a ground-in stopper, and was mixed by manual reciprocal shaking repeated 30 times, in the same manner as in Example 1. The entire solution was frozen immediately thereafter, and then subjected to lyophilization, which completely removed the water and the organic solvent.

Next, 2.0 ml of water was added to each of the lyophilized products obtained in this manner, the mixture was stirred and centrifuged, and then the solubility of the taxol in the supernatant was measured by high performance liquid chromatography (HPLC). The results thereof are shown in Table 2, along with the results of a case which was carried out in the same manner, but using 2.0 ml of ethyl acetate as the organic solvent in place of 2.0 ml of ethanol.

The conditions for HPLC were as follows.
Column: Crestpack (Jasco)
Solvent: Methanol:water=60:40
Flow rate: 1.0 ml/min
Column temperature: 40° C.
Detector: Ultraviolet detector

TABLE 2

Influence of solvent on the solubility of taxol in water

|  | Ethyl acetate | Ethanol |
|---|---|---|
| α-CD | 0.4 | 14.5 |
| γ-CD | 10.8 | 117.9 |
| Maltosyl-α-CD | 3.1 | 11.1 |
| Maltosyl-β-CD | 4.4 | 42.8 |
| Maltosyl-γ-CD | 8.1 | 38.0 |

(μg per mg of water)

Figure 2:
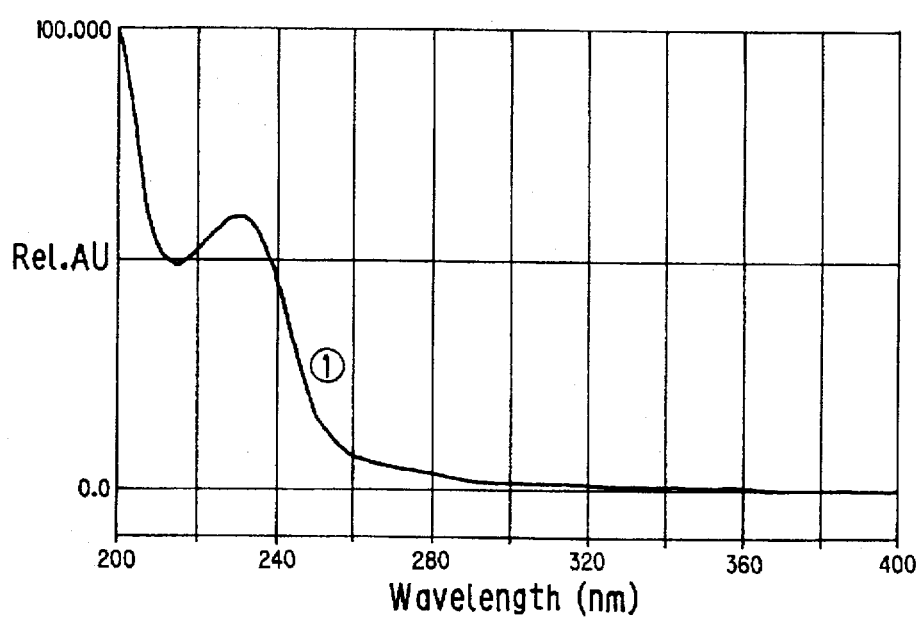
FIG. 2 shows an absorption spectrum of taxol.
Figure 3:
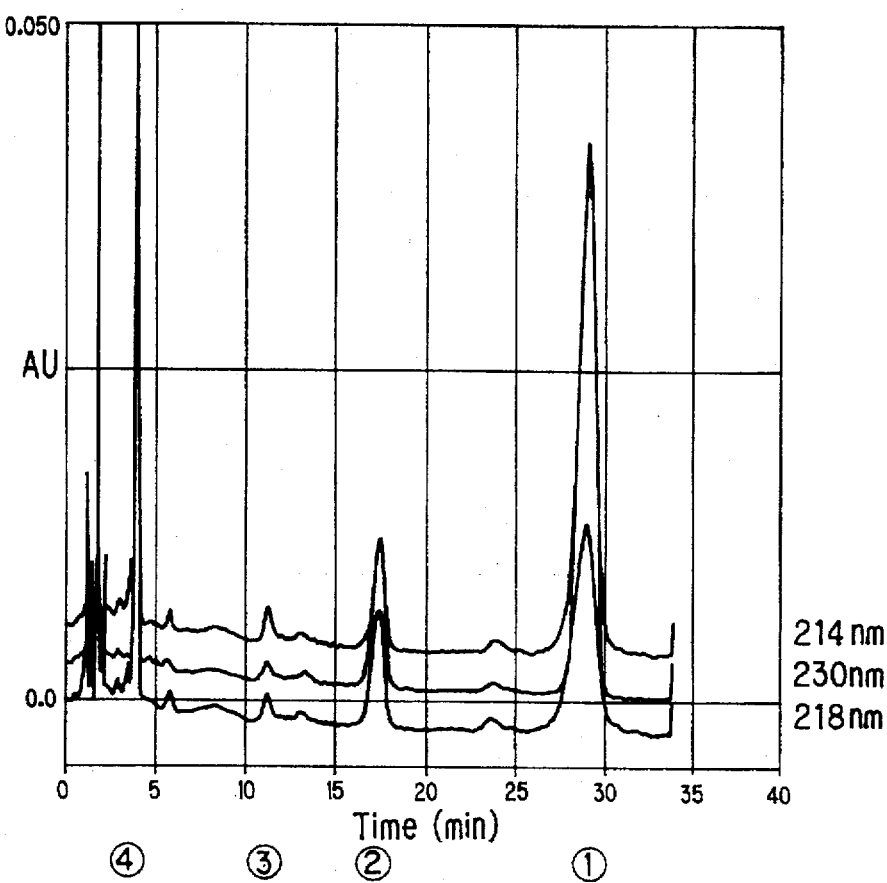
FIG. 3 shows an HPLC chromatogram of taxol—CD in a case where ethanol was used as the solvent according to Example 2.
Figure 4:
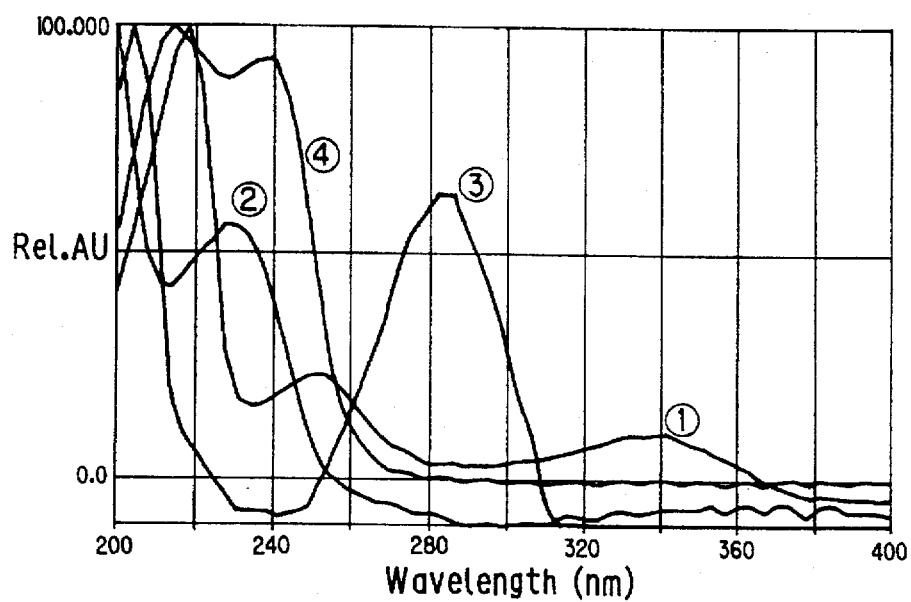
FIG. 4 shows an absorption spectrum of taxol—CD in a case where ethanol was used as the solvent according to Example 2.

For the taxol assay, the taxol itself untreated with CD was dissolved in ethyl acetate, and taxol solutions of various concentrations were prepared and their HPLC chromatograms were prepared. One example thereof is shown in FIG. 1, and the absorption spectrum is shown in FIG. 2. On the other hand, the HPLC chromatogram of a case where ethanol and γ-CD were used is shown in FIG. 3, and the absorption spectrums at each peak measured at the same times as indicated in FIG. 3 are shown in FIG. 4. The peak picking information for FIGS. 1 and 3 are given below.

|  | Time (min) | AUFS | Peak wavelength |
|---|---|---|---|
| FIG. 1 (1): | 17.27 | 0.078 | 230 |
| FIG. 3 (1): | 28.95 | 0.038 | 218 |
| FIG. 3 (2): | 17.27 | 0.015 | 230 |
| FIG. 3 (3): | 11.26 | 0.005 | 284 |
| FIG. 3 (4): | 3.86 | 0.036 | 214 |

Figure 5:
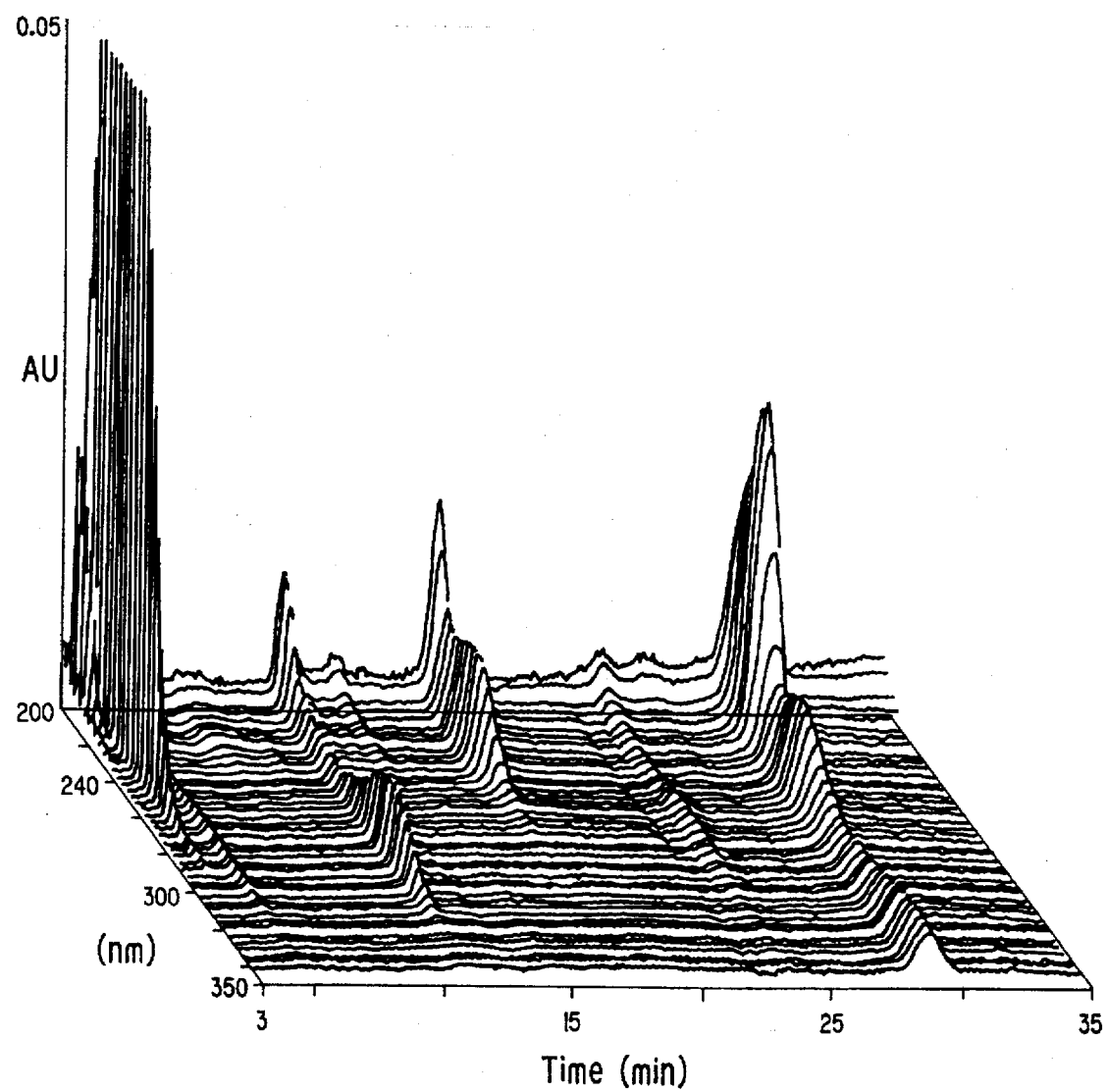
FIG. 5 shows a three-dimensional HPLC chromatogram of taxol-maltosyl-β-CD in a case where ethanol was used as the solvent according to Example 2.
Figure 6:
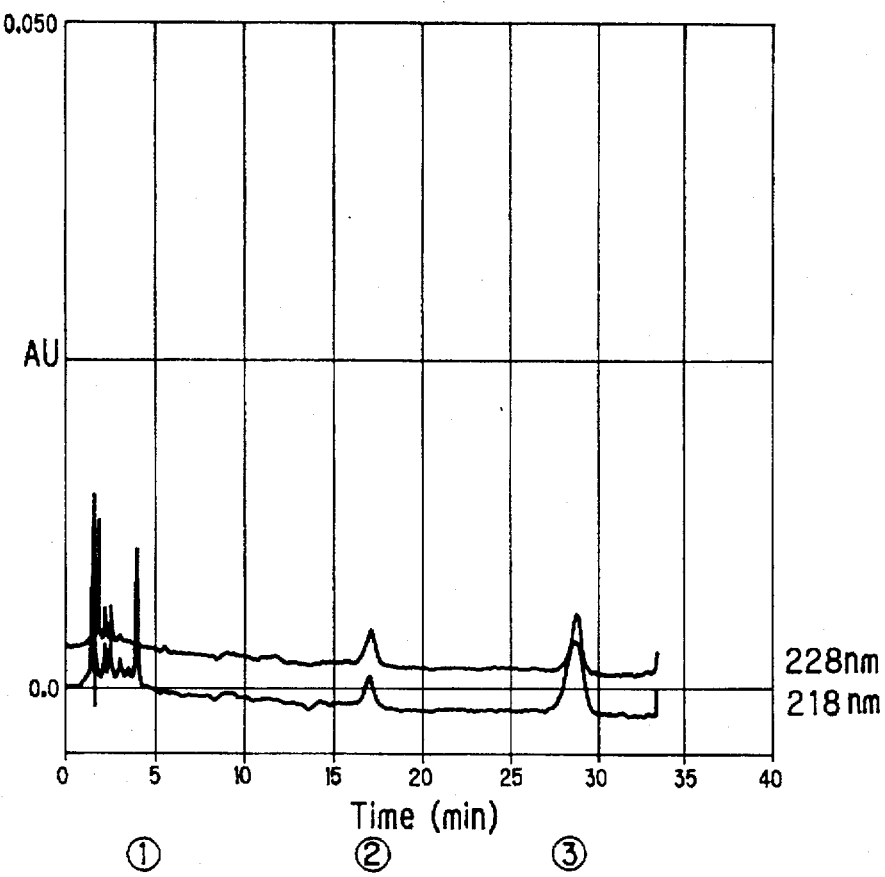
FIG. 6 shows an HPLC chromatogram of taxol-γ-CD in a case where ethyl acetate was used as the solvent and manual reciprocal shaking was effected according to Example 2.
Figure 7:
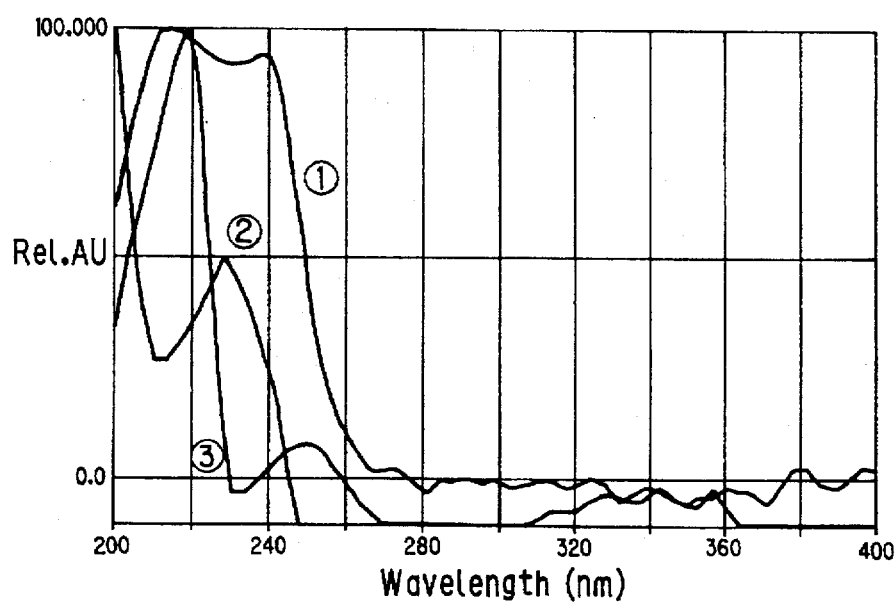
FIG. 7 shows an absorption spectrum of taxol-γ-CD in a case where ethyl acetate was used as the solvent and manual reciprocal shaking was effected according to Example 2.

In addition, a three-dimensional HPLC chromatogram of a case where ethanol and maltosyl-B-CD were used is shown in FIG. 5, and an HPLC chromatogram of a case where ethyl acetate and γ-CD were used is shown in FIG. 6. The absorption spectrum measured at each peak at the times indicated in FIG. 6 are shown in FIG. 7. The peak picking information for FIG. 6 is given below.

|  | Time (min) | AUFS | Peak wavelength |
|---|---|---|---|
| FIG. 6 (1): | 3.86 | 0.008 | 214, 238 |
| FIG. 6 (2): | 17.02 | 0.004 | 228 |
| FIG. 6 (3): | 28.78 | 0.006 | 218 |

As is clear from the above described Figures, the taxol to which the CD was added had a different retention time and a different absorption spectrum in HPLC, compared to taxol by itself. This fact indicates inclusion of the functional groups of taxol by the CD. It is thought that the CD forms an inclusion complex with the hydrophobic group of taxol, thus improving the solubility thereof. There was a greater improvement in the solubility when ethanol was used as the solvent for taxol, than when ethyl acetate was used. This is thought to be due to the changing of the conformation of taxol by the solvent. Even when ethanol was used as the solvent instead of ethyl acetate, γ-CD significantly improved the solubility of taxol, and was the most excellent solubilizer thereof.

Example 3

Figure 8:
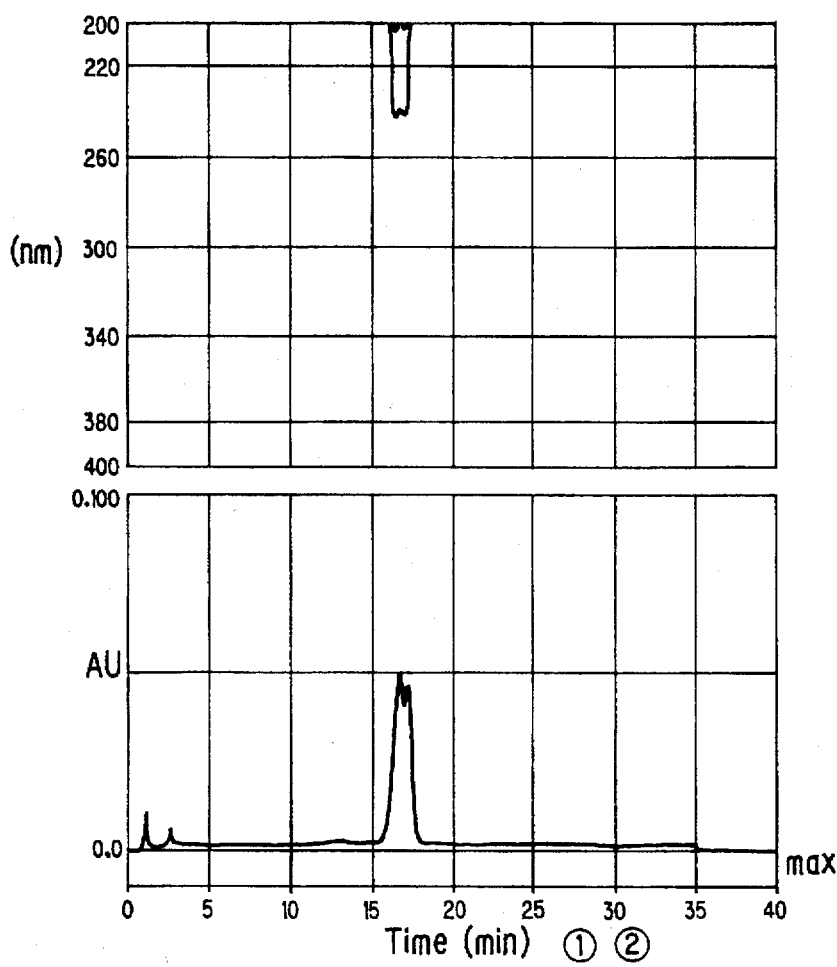
FIG. 8 shows an HPLC chromatogram of taxol-γ-CD in a case where ethyl acetate was used as the solvent and stirring was effected for one hour according to Example 3.
Figure 9:
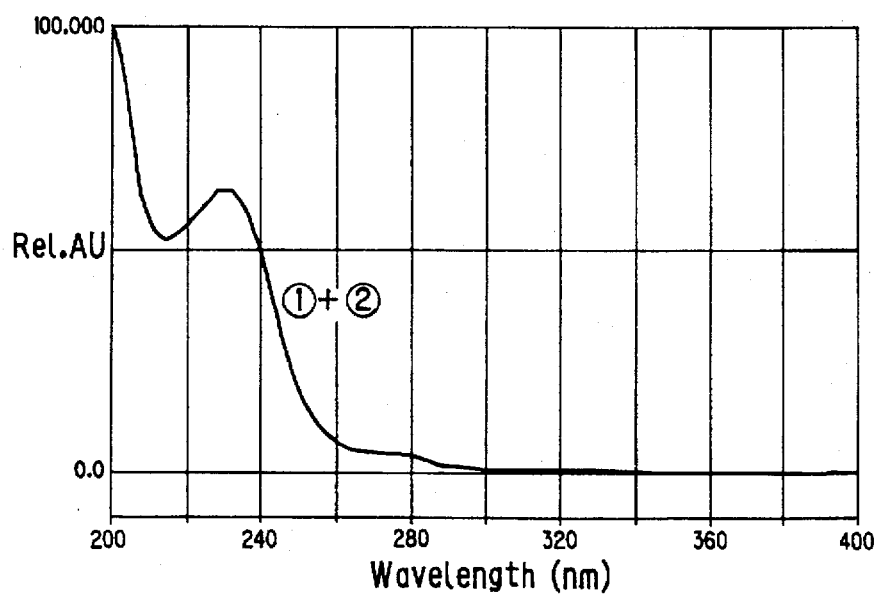
FIG. 9 shows an absorption spectrum of taxol-γ-CD in a case where ethyl acetate was used as the solvent and stirring was effected for one hour according to Example 3.

Twenty milligrams of taxol was dissolved in 40 ml of ethyl acetate, 200 mg of γ-CD was dissolved in 40 ml of water, and the two solutions were mixed and stirred for 1 hour with a stirrer. After allowing the mixture to stand, the aqueous layer was recovered and lyophilized. To the obtained dried product was added 40 ml of water, and the mixture was stirred for dissolution and subjected to centrifugation, after which the amount of taxol contained in the supernatant was measured using HPLC. The conditions for HPLC were the same as those in Example 2. The results are shown in FIG. 8, and the absorption spectrums measured at the respective peaks at the same times as indicated in FIG. 8 are shown in FIG. 9. The peak picking information for FIG. 8 is given below.

|  | Time (min) | AUFS |
|---|---|---|
| FIG. 8 (1): | 16.45 | 0.041 |
| FIG. 8 (2): | 17.19 | 0.046 |

The results indicated an amount of taxol of 81.5 µg per 1 mg of water. Comparing this to the result of 10.8 µg in Example 2 where manual reciprocal shaking was repeated 30 times, there was clearly a drastic increase in solubility. The reason for this is thought to be that the stirring time (reaction time) was 1 hour, or longer than in Example 2.

Further, when the HPLC chromatograms are compared, elution was effected at retention times 3.86, 17.02 and 28.78 minutes (FIG. 6) in the case where manual reciprocal shaking was effected, whereas elution was effected at 16.45 and 17.19 minutes (FIG. 8) in the case where stirring was effected for one hour. Further, the absorption spectrums converged at around 230 nm (FIG. 9). This was though to be due to the fact that a clathration equilibrium was reached with a certain proportion of CD forming inclusion complexes of the functional groups of taxol.

Thus, with a reaction time of one hour, a CD inclusion equilibrium may be reached, the solubility of taxol may be improved, and the solubilization of taxol may be generally increased.

As discussed above, according to the present invention, the solubility of taxol in water may be improved, and taxol may be solubilized, by adding a CD thereto at a molar ratio of 1–20 times with respect to taxol. Therefore, if a CD inclusion complex of taxol according to the present invention is used, taxol administered to cancer patients may be easily absorbed, and the physiological effects of taxol may be more effectively induced.

Example 4

Into water were dissolved 0.058 g of α-CD, 0.078 g of γ-CD, 0.078 g of 6-mono-0-maltosyl-α-CD (hereinafter referred to as $G_2$-α-CD), 0.088 g of 6-mono-0-maltosyl-β-CD (hereinafter referred to as $G_2$-β-CD), 0.097 g of 6-mono-0-maltosyl-γ-CD (hereinafter referred to as $G_2$-γ-CD), 0.069 g of 2,6-di-0-methyl-α-CD (hereinafter referred to as DM-α-CD), 0.080 g of 2,6-di-0-methyl-β-CD (hereinafter referred to as DM-β-CD), and 0.098 g of hydroxyethyl-β-CD in which, of 21 hydroxyl groups were contained in one β-CD molecule, an average of 1.6 groups were substituted through an ether bond with a hydroxyethyl group (hereinafter referred to as HE-β-CD) or 0.090 g of hydroxypropyl-β-CD in which, of 21 hydroxyl groups were contained in one β-CD molecule, an average of 0.9 groups were substituted through an ether bond with a hydroxypropyl group (hereinafter referred to as HP-β-CD), and the volume of each solution was adjusted to 10 ml to prepare aqueous CD solutions of a concentration of 6 mM.

To the solutions were added 2 mg each of taxol, and the resulting mixtures were stirred at room temperature (20° to 25° C.) at 5,000 r.p.m. As a control, 2 mg of taxol were added to 10 ml of water, and the resulting mixture was stirred at room temperature (20° to 25° C.) at 5,000 r.p.m. After 70 minutes of stirring, the solutions were passed through a filter of a pore diameter of 0.45 µm, and the concentration of taxol contained in the filtrates was determined by high performance liquid chromatography (HPLC). The results obtained are shown in Table 3.

TABLE 3

|  | Solubility of Taxol (µg/ml) |
|---|---|
| CD not added (Control) | 0 |
| α-CD | 0.3 |
| γ-CD | 0.3 |
| $G_2$-α-CD | 0.3 |
| $G_2$-β-CD | 0.5 |
| $G_2$-γ-CD | 0.4 |
| DM-α-CD | 2.8 |
| DM-β-CD | 47.1 |
| HE-β-CD | 0.5 |
| HP-β-CD | 1.1 |

Example 5

Into water were dissolved 1,296 g of $G_2$-α-CD, 1.458 g of $G_2$-β-CD, 1,620 g of $G_2$-γ-CD-, 1.331 g of DM-β-CD, 1.429 g of 2,3,6-tri-O-methyl-β-CD (hereinafter referred to as TM-β-CD), and 1.629 g of HE-β-CD or 1.501 g of HP-β-CD, and the volume of each solution was adjusted to 10 ml to prepare aqueous CD solutions of a concentration of 100 mM. Then, 20 mg of taxol were added to the aqueous DM-β-CD solution, 2 mg of taxol to the aqueous HP-β-CD solution, and 1 mg each of taxol to the other aqueous CD solutions, and the resulting mixtures were stirred at room temperature (20° to 25° C.) at 5,000 r.p.m. As a control, 1 mg of taxol was added to 10 ml of water, and the resulting mixture was stirred at room temperature (20° to 25° C.) at 5,000 r.p.m. After 70 minutes of stirring, the solutions were passed through a filter with a pore diameter of 0.45 µm, and the concentration of taxol contained in the filtrates was determined. The results obtained are shown in Table 4.

TABLE 4

|  | Solubility of Taxol (µg/ml) |
|---|---|
| CD not added (Control) | 0.4 |
| $G_2$-α-CD | 1.6 |
| $G_2$-β-CD | 23.0 |
| $G_2$-γ-CD | 1.5 |
| DM-β-CD | 1236 |
| TM-β-CD | 28.0 |
| HE-β-CD | 22.0 |
| HP-β-CD | 68.9 |

Example 6

Figure 10:
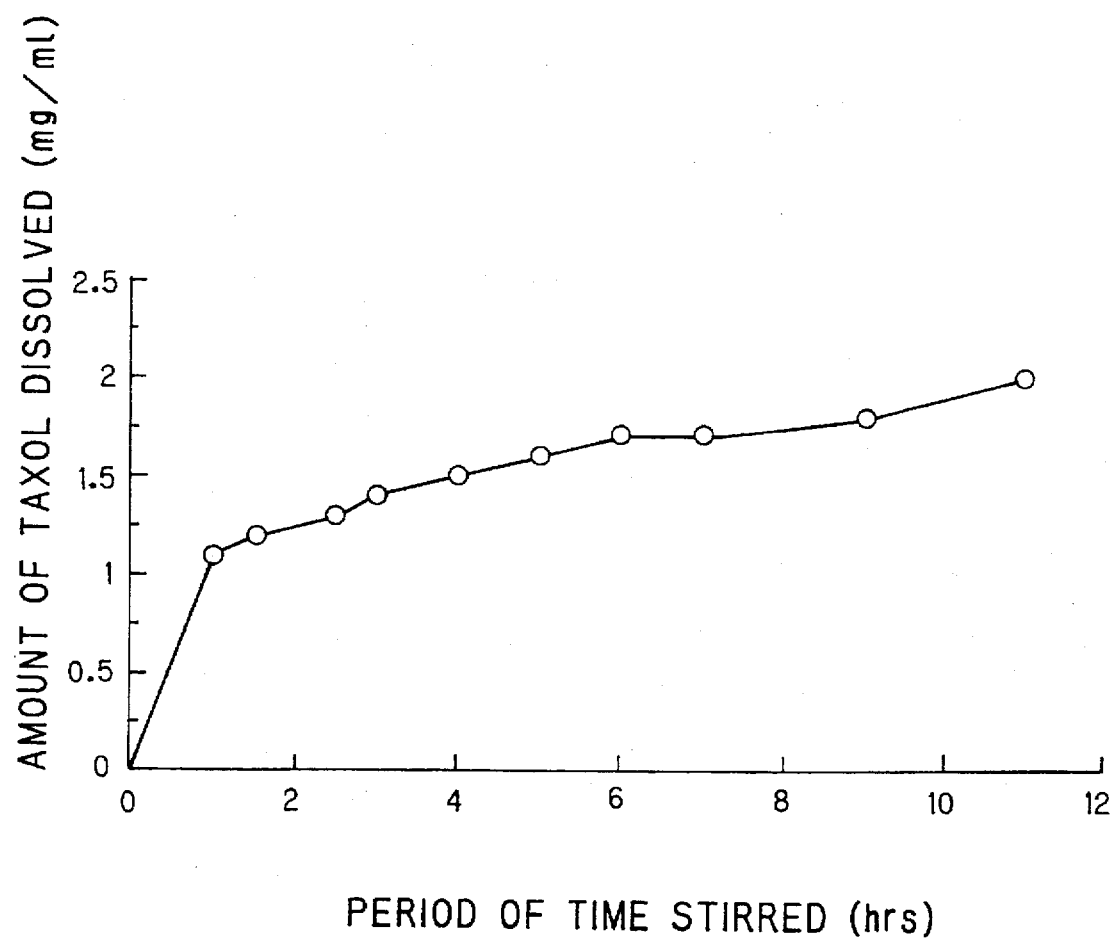
FIG. 10 is a graph showing the change with the lapse of time of the amount of taxol dissolved into an aqueous 0.1M solution of 2,6-di-O-methyl-β-CD (DM-β-CD).

Into water was dissolved 1.331 g of DM-β-CD, and the volume of the solution was adjusted to 10 ml to prepare an aqueous CD solution of a concentration of 100 mM. To this were added 20 mg of taxol, and the resulting mixture was stirred at room temperature (20° to 25° C.) at 5,000 r.p.m. for a period of 11 hours. While stirring, samples of the mixture were taken at appropriate intervals and passed through a filter with a pore size of 0.45 μm, and the concentration of taxol contained in the filtrates was determined. The results obtained are shown in FIG. 10.

Example 7

Into 70 ml of a mixture of methanol and water (volume ratio, 1:1), the same volume of a mixture of acetonitrile and water (volume ratio, 1:1), the same volume of a mixture of acetone and water (volume ratio, 1:1) and the same volume of mixture of tetrahydrofuran and water (volume ratio, 1:1) were added 5 mg each of taxol. To the resulting taxol solutions were added 500 mg each of DM-β-CD, and the resulting mixtures were stirred vigorously by a stirrer at a temperature of 25° C. After two hours of stirring, 100 ml each of water were added thereto, and the resulting solutions were freeze-dried, so as to obtain powders by completely removing the water and the organic solvents. Then, 8 mg each of the thus-obtained powders were dissolved into 1 ml of water while stirring, and the resulting solutions were passed through a filter with a pore size of 0.45 μm, and the concentration of DM-β-CD and of the taxol contained in the filtrates was determined by HPLC. Table 5 shows the solubility of taxol at a DM-β-CD concentration of 6 mM.

TABLE 5

| Organic Solvent Used | Solubility of Taxol (μg/ml) |
| --- | --- |
| Methanol | 63.2 |
| Acetonitrile | 78.6 |
| Acetone | 43.9 |
| Tetrahydrofuran | 10.3 |

Example 8

Two taxol solutions were prepared by dissolving 5 mg each of taxol into 100 ml each of mixtures of methanol and water (volume ratio, 1:1). To these solutions were added 50 mg of HE-β-CD or HP-β-CD, and the resulting mixtures were vigorously stirred using a stirrer at 25° C. After 2 hours of stirring, 300 ml of water were added thereto, and the resulting solutions were subjected to freeze-drying, so as to obtain powders by completely removing the water and the organic solvent.

Parts of the thus-obtained powders (9.8 mg of HE-β-CD and 9.0 mg of HP-β-CD) were dissolved into 1 ml each of water. After being stirred, the resulting mixtures were passed through a filter with a pore size of 0.45 μm, and the concentration of taxol contained in the filtrates was determined. The results obtained are shown in Table 6.

TABLE 6

| CD Used | Solubility of Taxol (μg/ml) |
| --- | --- |
| HE-β-CD | 1.3 |
| HP-β-CD | 6.1 |

Example 9

13.31 g of DM-β-CD was dissolved into water and the volume of the solution was adjusted to 100 ml to prepare aqueous CD solution of a concentration of 0.1M.

To the solution was added 1.2 g of taxol, and the resulting mixtures was stirred by a stirrer at 25° C.; for 1 hour. Subsequently, the mixture was filtered with a membrane filter having a pore size of 0.45 μm to remove the undissolved taxol, thereby a transparent solution was obtained. The resulting solution was freeze-dried to obtain taxol DM-β-CD complex in powder form.

0.05 g of taxol-DM-β-CD complex powder was dissolved into water to make 10 ml of solution. Then, 20 μl of the solution was subjected to HPLC analysis under the following conditions: column: Crest Pak C18S (JASCO Co., Japan), column temperature: room temperature, eluent: methanol/water=65/35 (by volume), flow rate: 1.0 ml/min., detector: UV detector, and measured wave length: UV 230 nm. As the standard solutions of taxol, 50 μg/ml, 100 μg/ml, 150 μg/ml, and 200 μg/ml of taxol solution dissolved in methanol/water (65/35 by volume) were prepared, and 20 μl of each of these solutions was analyzed under the same analytical conditions as above to obtain a calibration curve. According to the absolute calibration curve method, taxol content in the taxol-DM-β-CD complex powder was determined to be 10.7 mg/g-powder.

Taxol-DM-β-CD complex powder, taxol, and DM-β-CD were dissolved into $D_2O$ or $d_6$-DMSO. The resultant solution was subjected to $^1$H-NMR (400 MHz) or $^{13}$C-NMR (100 MHz) analysis with the use of JNM-GSX 400 spectrometer (manufactured by JEOL. Ltd.). The results are shown in FIGS. 11 to 17.

Figure 11:
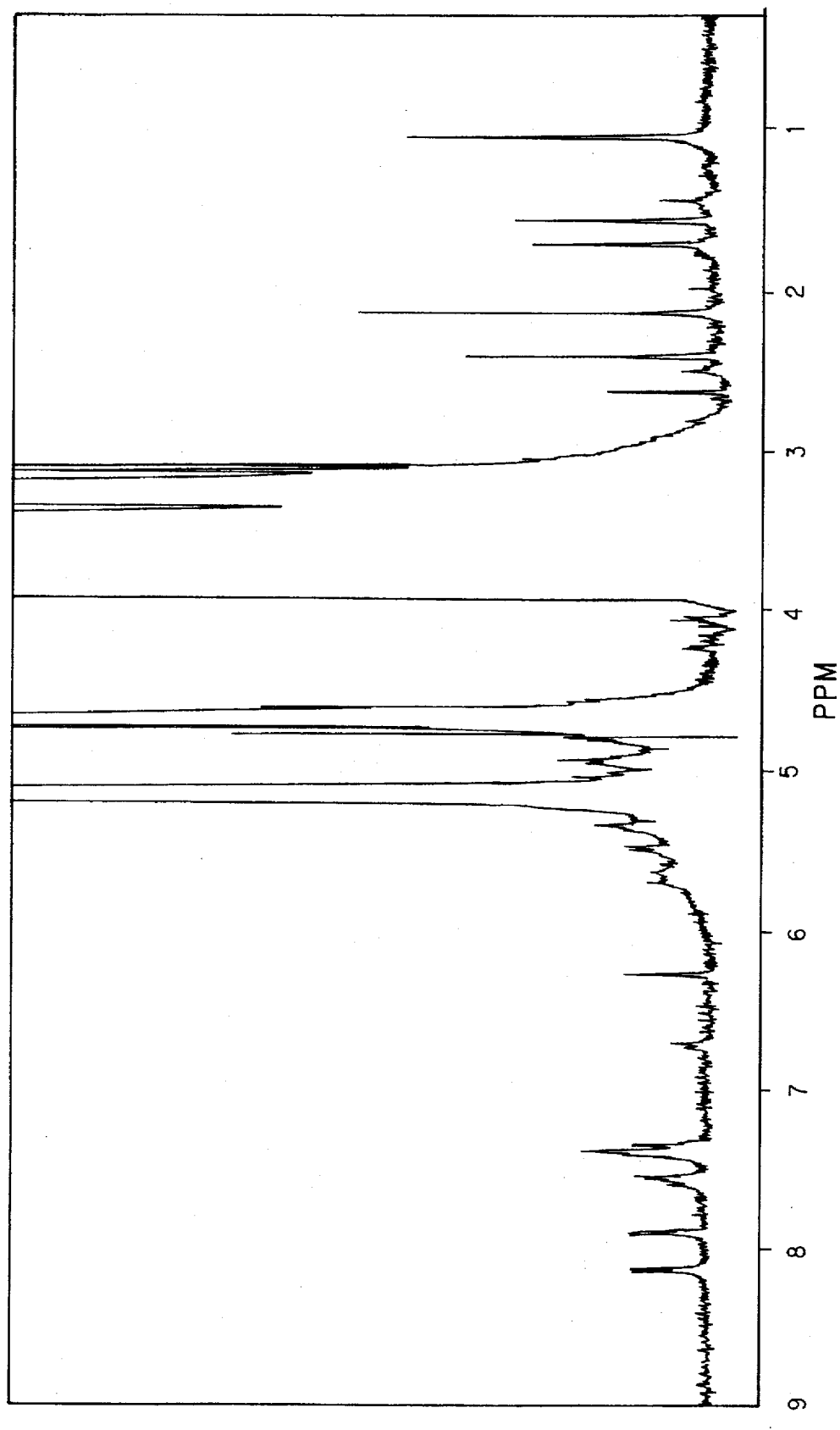
FIG. 11 is a spectrum of a $^1$H-NMR analysis for taxol-DM-β-CD complex powder dissolved in $D_2O$.
Figure 12:
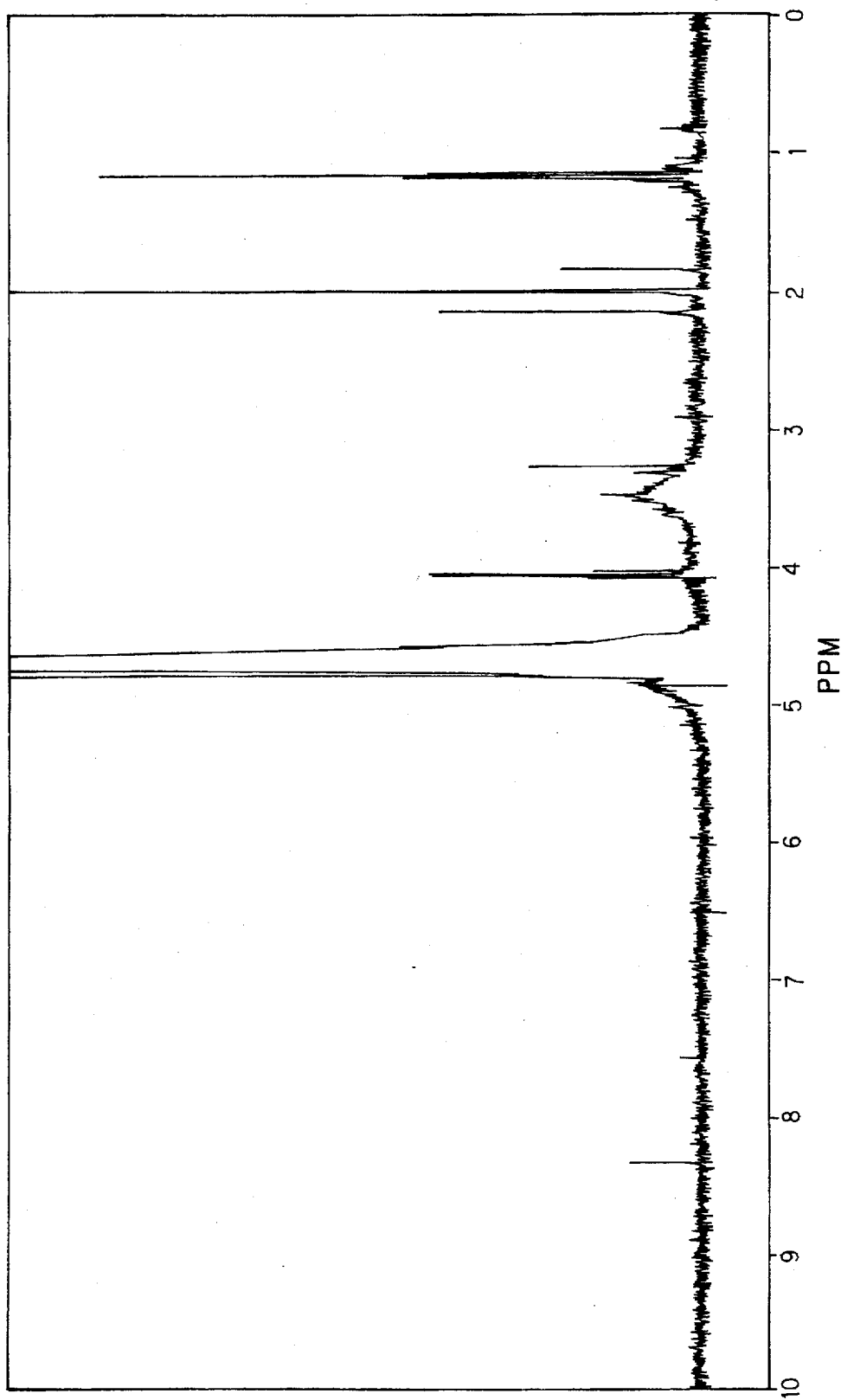
FIG. 12 is a spectrum of a $^1$H-NMR analysis for taxol dissolved in $D_2O$.

FIGS. 11 and 12 are spectra of $^1$H-NMR analysis for taxol-DM-β-CD complex powder and taxol dissolved in $D_2O$, respectively. A spectrum of taxol is clear in FIG. 11, but not in FIG. 12.

Figure 13:
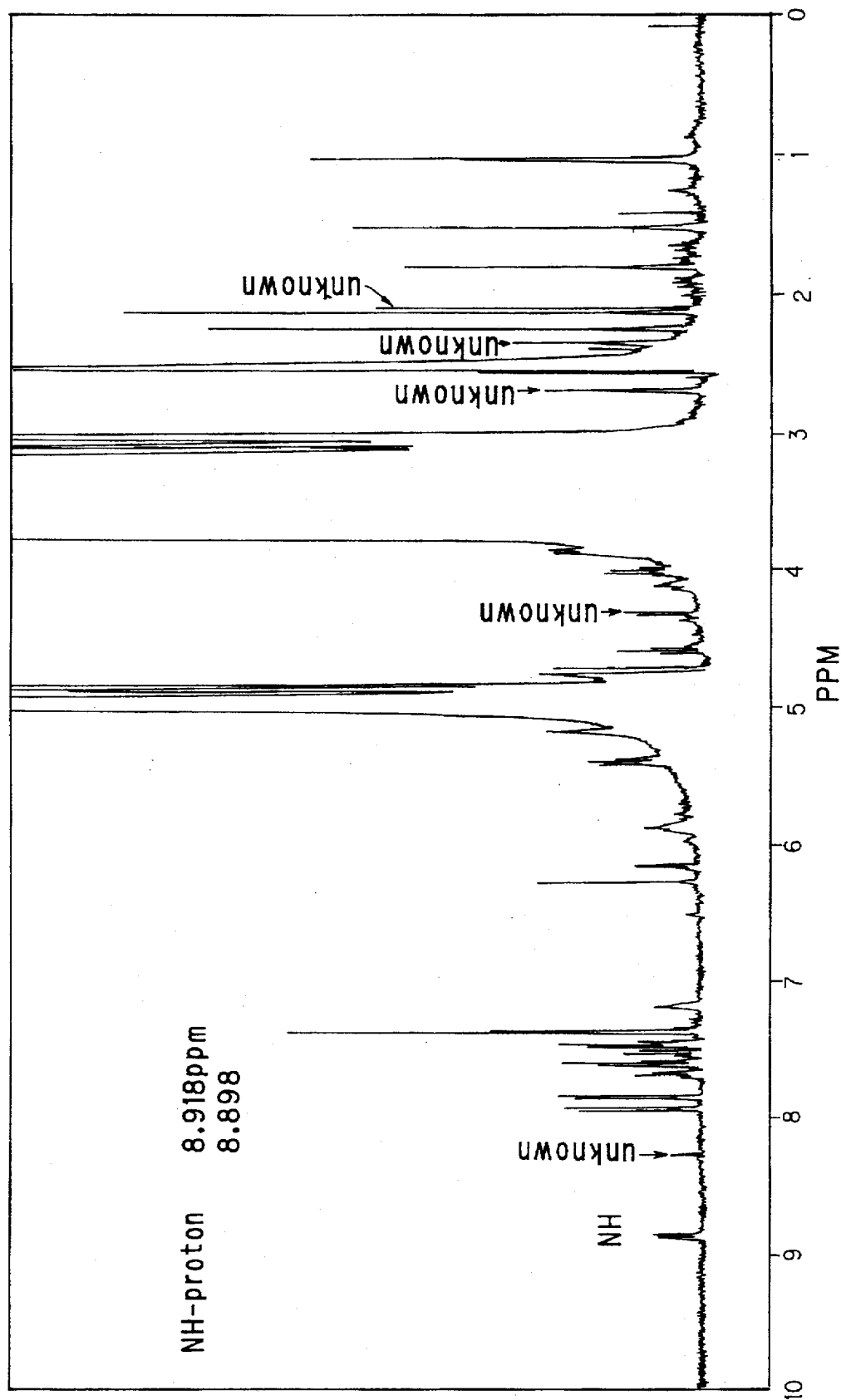
FIG. 13 is a spectrum of a $^1$H-NMR analysis for taxol-DM-β-CD complex powder dissolved in $d_6$-DMSO.
Figure 14:
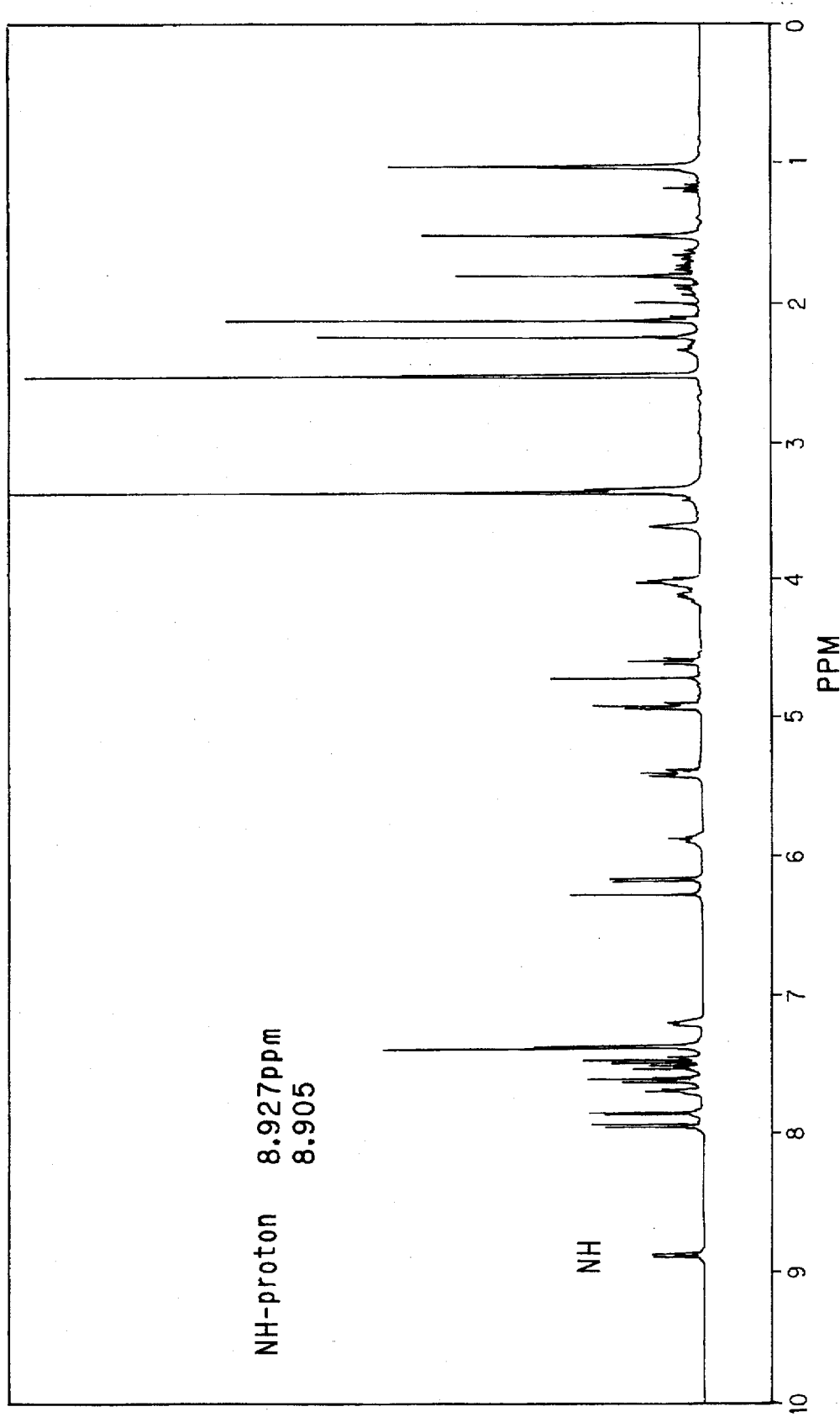
FIG. 14 is a spectrum of a $^1$H-NMR analysis for taxol dissolved in $d_6$-DMSO.
Figure 15:
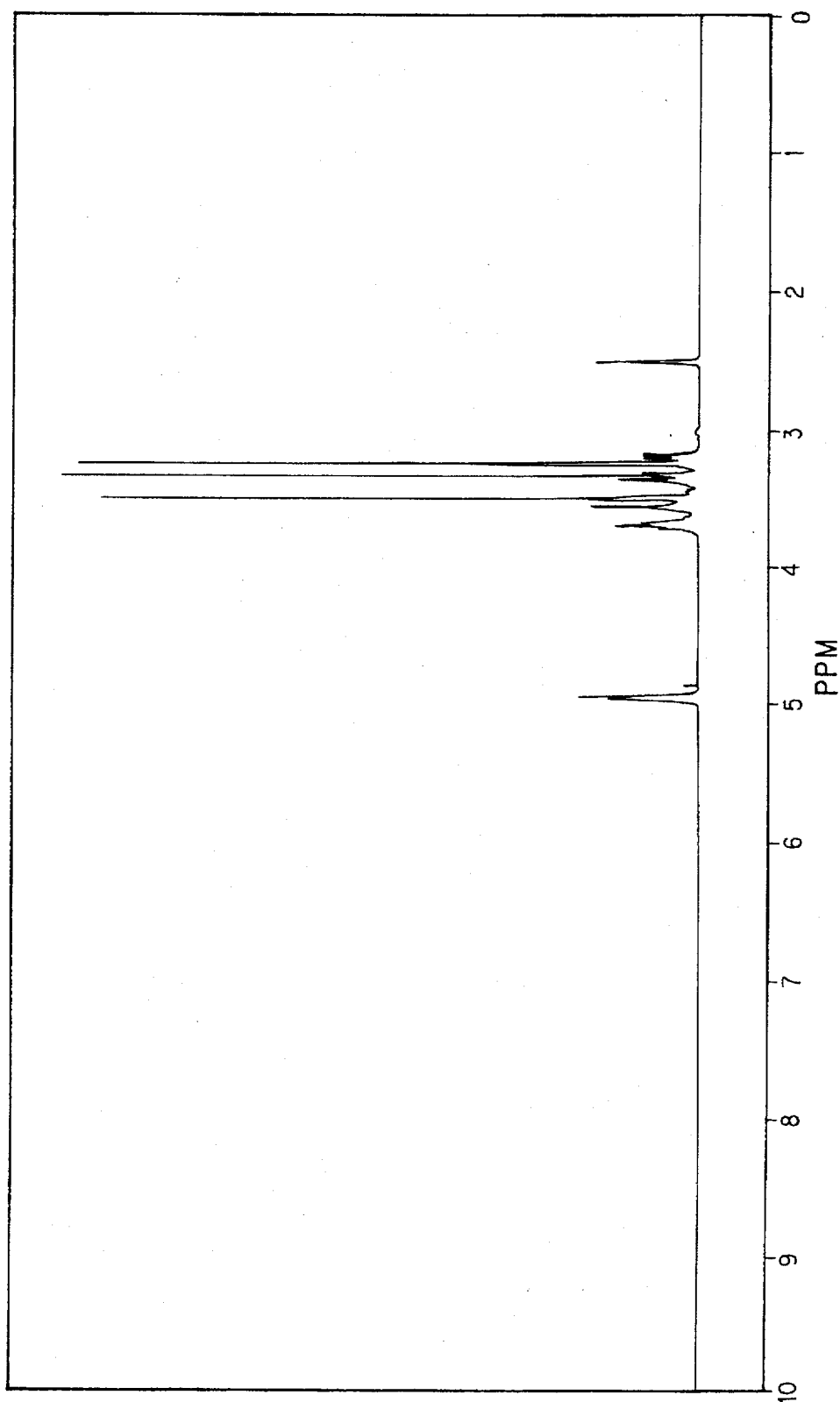
FIG. 15 is a spectrum of a $^1$H-NMR analysis for DM-β-CD dissolved in $d_6$-DMSO.
Figure 16:
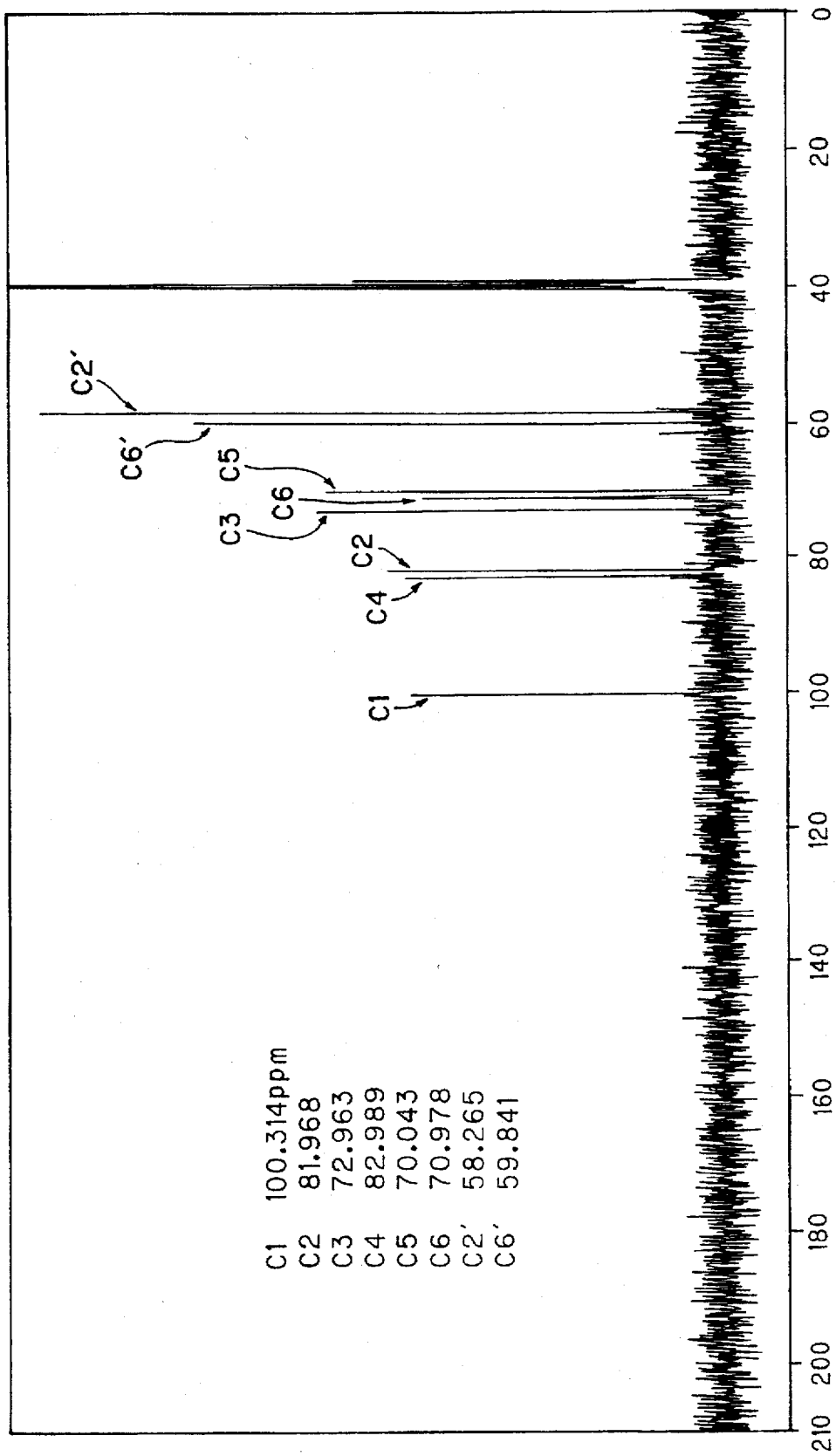
FIG. 16 is a spectrum of a $^{13}$C-NMR analysis for taxol-DM-β-CD complex powder dissolved in $d_6$-DMSO.
Figure 17:
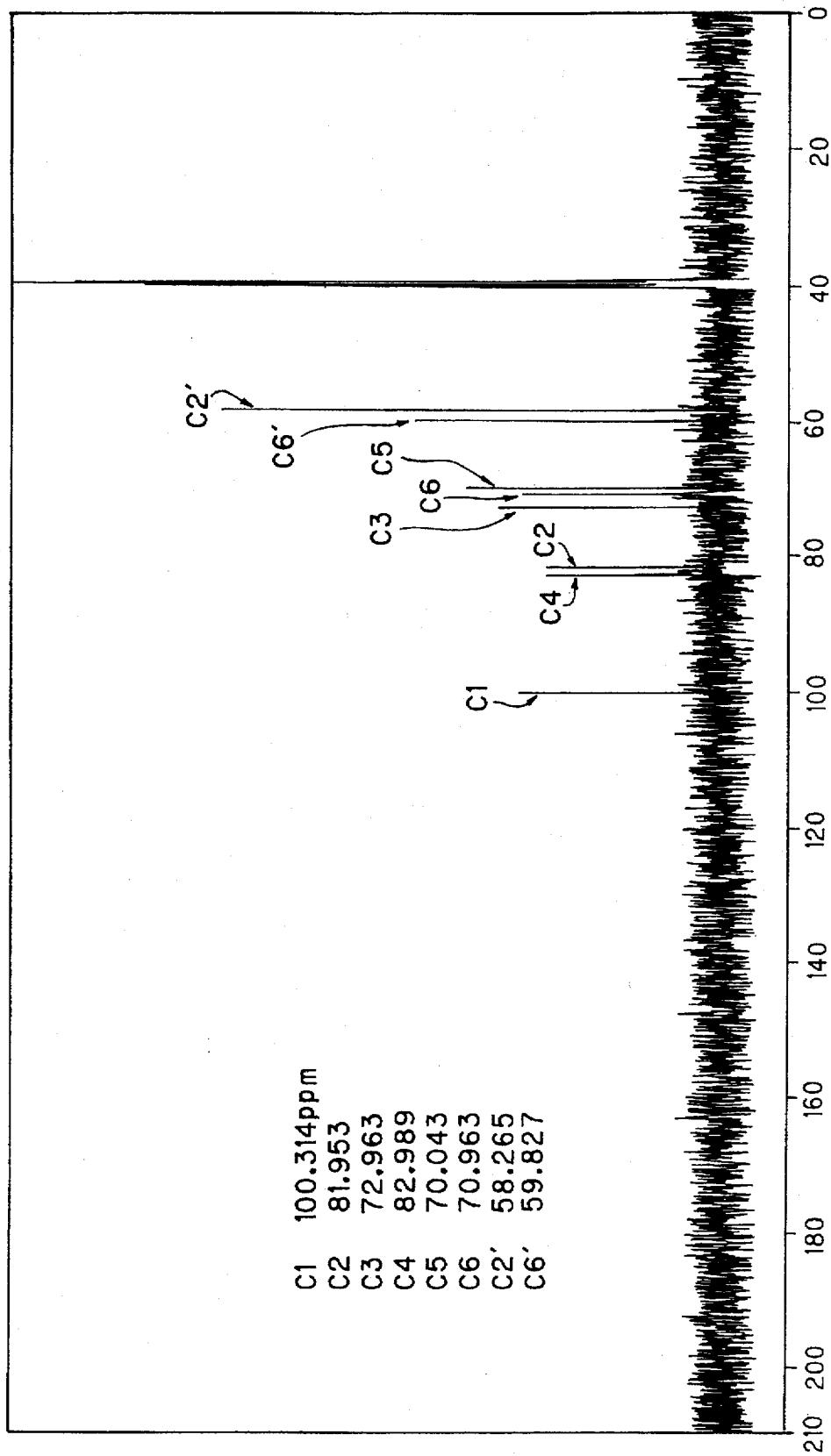
FIG. 17 is a spectrum of a $^{13}$C-NMR analysis for DM-β-CD dissolved in $d_6$-DMSO.

FIGS. 13, 14 and 15 are spectra of $^1$H-NMR analysis for taxol-DM-β-CD complex powder, taxol and DM-β-CD each dissolved in $d_6$-DMSO, respectively. By comparing each chemical shift of taxol in the taxol-DM-β-CD complex and free taxol, it was found that NH proton among signals of taxol in the taxol-DM-β-CD complex was shifted upstream, and in the spectrum of taxol in the taxol-DM-β-CD complex there were existed signals different from these of the spectrum of free taxol. FIGS. 16 and 17 are spectra of $^{13}$C-NMR analysis for taxol-DM-β-CD complex powder and for DM-β-CD dissolved in $d_6$-DMSO, respectively. By comparing each chemical shift of DM-β-CD in the taxol-DM-β-CD complex and free DM-β-CD, it was found that C-2, C-6 and C-6' (carbon of methoxyl group) in the glucose unit of CD in the taxol-DM-β-CD complex were shifted downstream.

By the above results, it was found that the solubility of taxol to water was improved by the existence of CD, and thus the interaction between taxol and DM-β-CD was suggested.

What is claimed is:

1. A method for the production of a cyclodextrin inclusion complex of taxol, comprising adding 2,6-di-O-methyl-β-cyclodextrin to taxol at a molar ratio of 1–20 times, with respect to said taxol.

2. A method for the improvement of the solubility of taxol comprising:

adding taxol to an aqueous solution of 2,6-di-O-methyl-β-cyclodextrin at a molar ratio of 1–20, times with respect to said taxol, and then stirring or shaking.

3. The method of claim 1, wherein the method is carried out for 2 minutes to one hour.

4. The method of claim 2, wherein the method is carried out for 2 minutes to one hour.

5. The method of claim 1, wherein the molar ratio is 1:1.
6. The method of claim 1, wherein the molar ratio is 1:5.
7. The method of claim 1, wherein the molar ratio is 1:10.
8. A method for producing an inclusion product of taxol included in a cyclodextrin, which method comprises:

dissolving taxol in a solvent, said solvent being selected from the group consisting of (i) acetonitrile and water in a volume ratio of 1:1, (ii) acetone and water in a volume ratio of 1:1 and (iii) methanol and water in a volume ratio of 1:1, and then adding 2,6-di-O-methyl-β-cyclodextrin, while stirring or shaking.

9. A method for improving the solubility of taxol, which comprises:

dissolving taxol in a solvent, said solvent being selected from the group consisting of (i) acetonitrile and water in a volume ratio of 1:1, (ii) acetone and water in a volume ratio of 1:1 and (iii) methanol and water in a volume ratio of 1:1, and then adding 2,6-di-O-methyl-β-cyclodextrin, while stirring or shaking.

10. The method of claim 2, wherein said 2,6-di-O-methyl-β-cyclodextrin is in a concentration of 0.0001 to 200% by weight, based on the weight of water.

11. The method of claim 2, wherein said 2,6-di-O-methyl-β-cyclodextrin is in a concentration of 1 to 50% by weight, based on the weight of water.

12. The method of claim 2, wherein said 2,6-di-O-methyl-β-cyclodextrin is in a concentration of 1 to 100,000,000 times the mole amount of the taxol.

13. The method of claim 11, wherein the 2.6-di-O-methyl-β-cyclodextrin is in an amount of 100 to 100,000 times the mole amount of the taxol.

14. The method of claim 2, wherein the reaction is carried out at a temperature of 0° to 60° C.

15. The method of claim 13, wherein the reaction is carried out at a temperature of 15° to 40° C.

16. A 2,6-di-O-methyl-β-cyclodextrin inclusion complex of taxol.

17. The method of claim 2, wherein the molar ratio is 1:1.

18. The method of claim 2, wherein the molar ratio is 1:5.

19. The method of claim 2, wherein the molar ratio is 1:10.

* * * * *